United States Patent [19]

Baldo et al.

[11] Patent Number: 5,061,626
[45] Date of Patent: Oct. 29, 1991

[54] ANTIGENIC ANAROGUES OF PLATELET ACTIVATING FACTOR

[75] Inventors: Brian A. Baldo, Pymble; John W. Redmond, West Ryde, both of Australia

[73] Assignee: University of Sydney, Sydney, Australia

[21] Appl. No.: 156,923

[22] PCT Filed: Mar. 24, 1987

[86] PCT No.: PCT/SU87/00084

§ 371 Date: Nov. 24, 1987

§ 102(e) Date: Nov. 24, 1987

[87] PCT Pub. No.: WO87/05904

PCT Pub. Date: Oct. 8, 1987

[30] Foreign Application Priority Data

Mar. 24, 1986 [AU] Australia .................. PH5175

[51] Int. Cl.$^5$ .................. C12N 11/00; C07K 17/00; C07F 9/09; G01N 33/532
[52] U.S. Cl. .................. 435/174; 260/403; 435/192; 435/1991207; 436/545; 436/546; 530/345; 530/402; 530/403; 530/404; 530/406; 530/408; 530/409; 530/410; 558/169; 558/172
[58] Field of Search .............. 530/405, 406, 409, 410, 530/345, 402, 403, 404, 408; 558/172, 169; 260/403; 435/174, 192, 545, 546, 199, 207

[56] References Cited

U.S. PATENT DOCUMENTS

| | | | |
|---|---|---|---|
| 3,708,558 | 1/1973 | Kny | 558/169 |
| 4,329,302 | 5/1982 | Hanahan | 558/169 |
| 4,370,311 | 1/1983 | Ilekis | 436/13 |
| 4,551,446 | 11/1985 | Hanahan et al. | 514/77 |
| 4,965,391 | 10/1990 | Counsell et al. | 558/169 |

FOREIGN PATENT DOCUMENTS 1169433 6/1984 Canada .................. 514/114

OTHER PUBLICATIONS

Nishihira et al., (1984), J. Biochem. 95:1247-1251.
Rifai et al., (1986), J. Immunol. Methods 94:25-30.
Karasawa et al., (1987), J. Biochem. 102:451-453.
Journal of Immunology, vol. 134, No. 2, (1985) M. Oda et al., "Molecular Species of Platelet-Activating Factor Generated by Human Neutrophils Challenged with Ionophore A 23187", pp. 1090-1093.
Patent Abstracts of Japan, C-9, p. 117, JP 55-28955 (Toyama Kogaku Kogyo K.K.) 29 Feb. 1980.
Chemical Abstracts, vol. 104, No. 5 issued 1986, Lakin K. et al., "Activation of Rabbit Platelets induced by 1-0-alkyl-2-0-acetyl-sn-glycerophospho line", see p. 388, abstract No. 32325s, Byull, Eksp. Biol., Med., 1985 100 (10) 410-412 (Russ).

*Primary Examiner*—Jeffrey E. Russel
*Assistant Examiner*—Kay Kim

[57] ABSTRACT

The invention concerns antigens for the production of antibodies to Platelet Activating Factor (PAF). The antigens are PAF analogues of formula (I)

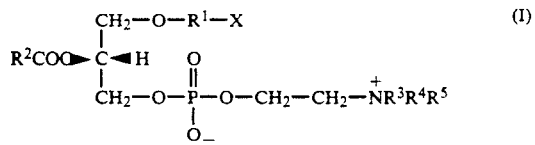

wherein X comprises a high molecular weight group, $R^1$ is a linking group and $R^2$ to $R^5$ are selected from $C_1$ to $C_6$ alkyl.

Other aspects of the invention include PAF-antibodies produced using said antigens, labelled PAF analogues, intermediates for the preparation of PAF analogues and methods and a kit for the immunoassay of PAF.

8 Claims, No Drawings

ANTIGENIC ANAROGUES OF PLATELET ACTIVATING FACTOR

TECHNICAL FIELD

The present invention relates to novel antigens capable of producing antibodies to Platlet Activating Factor (PAF), novel PAF analoques labelled to enable quantitative assay, intermediates for the production of novel PAF antigens and methods for the preparation of said antigens, and methods of immunoassay of PAF in biological fluid using said labelled analogues and/or labelled PAF-antibodies.

BACKGROUND

Platelet Activating Factor (PAF), 1-O-alkyl-2-O-acetyl-sn-glycero-3-phosphocholine, represents a recently defined example of a class of biologically-active lipids active in the subnanomolar range and possessing a wide spectrum of pathophysiological effects. PAF promotes life-threatening anaphylactic reactions in animals and is suspected of mediating a range of allergic and inflammatory reactions in man. For example, PAF may be important in conditions such as asthma, adult respiratory distress syndrome and shock reactions. However, despite the increasing catalogue of conditions in which PAF maybe involved, greater insights into its role in health and disease ar hampered because precise and specific methods for its measurement are lacking. The capacity of PAF to aggregate platelets does not provide a suitable basis for strictly quantitative assay.

It would be desirable to develop an immunoassay for quantitative determination of PAF levels in blood serum. However, it has been found that PAF itself is insufficiently antigenic to produce the necessary PAF-antibodies needed for such an immunoassay.

Novel synthetic PAF analogues have now been found which are sufficiently antigenic to produce PAF-antibodies and a method suitable for the immunoassay of PAF levels in biological fluids has been developed.

THE INVENTION

Accordingly the invention provides novel compounds of general formula (I)

$$\begin{array}{l}CH_2-O-R^1-X\\ R^2COO-C\blacktriangleleft H\quad O\\ \phantom{R^2COO-}|\phantom{-C\blacktriangleleft H}\parallel\\ CH_2-O-P-O-CH_2-CH_2-\overset{+}{N}R^3R^4R^5\\ \phantom{CH_2-O-}|\\ \phantom{CH_2-O-}O_-\end{array}$$

wherein:
(1) $R^1$ is a $C_2$ to $C_{25}$ alkylene or alkenylene linking group substituted by radioactive iodine;
X is hydrogen; or
(2) $R^1$ is a $C_2$ to $C_{25}$ alkylene, alkenylene or alkynylene linking group optionally substituted by tritium or radioactive iodine;
X is selected from:
(a) the group consisting of formyl, di($C_1$ to $C_6$ alkoxy)methyl, carboxy, isothiocyanato, N—$C_1$ to $C_6$ alkylamino, N,N-di($C_1$ to $C_6$ alkyl)amino, hydroxy and mercapto; and
(b) the group —A—B wherein A is a linking group selected from the groups —$NR^6$—, —COO—, —OCO—, —$CONR^6$—, —$NR^6CO$—, —NH—C—S—NH—and —S—S—wherein $R^6$ is selected from hydrogen and $C_1$ to $C_6$ alkyl; and
B is selected from:
(i) monofunctional and polyfunctional protein peptide, carbohydrate and lipid groups and derivatives thereof of molecular weight of at least 2000; and
(ii) a label; and
$R^2$ to $R^5$ are independently selected from $C_1$ to $C_6$ alkyl; and mixtures of the compound of formula (I) and its enantiomer.

In one embodiment the invention provides antigenic PAF analogues of general formula (I) wherein:
$R^1$ is a $C_2$ to $C_{25}$ alkylene or alkenylene linking group;
X is the group —A—B wherein:
A is a linking group selected from —$NR^6$—, —COO—, —OCO—, —$CONR^6$—, —$NR^6CO$— —and —S—S—wherein $R^6$ is selected from hydrogen and $C_1$ to $C_6$ alkyl; and
B is selected from monofunctional and polyfunctional protein, peptide, carbohydrate and lipid groups and derivatives thereof of molecular weight of at least 2000 which are capable of eliciting an antigenic response; and
$R^2$ to $R^5$ are independently selected from $C_1$ to $C_6$ alkyl.

In the antigenic PAF analogues of the invention of general formula (I):
Preferred $R^1$ include straight chain $C_4$ to $C_{16}$ alkylene. More preferred $R^1$ include straight chain $C_4$ to $C_8$ alkylene. For convenience $R^1$ is often chosen from pentylene and hexylene.
Preferred A include —$NR^6$—, —COO—, —OCO—, —$CONR^6$—and $R^6CO$—and preferred $R^6$ include hydrogen and methyl. More preferred A include —$NR^6$—and —OCO—.
Preferred B include monofunctional and polyfunctional protein, peptide, carbohydrate and lipid groups of molecular weight at least 5000 and capable of eliciting an antigenic response. More preferred B include monofunctional and polyfunctional groups of molecular weight at least 10,000. Examples of suitable B include Bovine Serum Albumin (BSA), ovalbumin, Porcine Thyroglobulin (PTG), Bovine Thyroglobulin (BTG), keyhole limpet hemocyanin, bacterial cell walls, synthetic polypeptides such as polylysine, poke weed mitagen (PWM), phytohaemoglutinin (PHA), muramyl dipeptidase and lipopolysaccharides.
Preferred $R^2$ to $R^5$ include $C_1$ to $C_3$ alkyl, and especially methyl.

In another embodiment the invention provides labelled PAF analogues of general formula (I) wherein:
(1) $R^1$ is a $C_2$ to $C_{25}$ alkylene or alkenylene linking group substituted by radioactive iodine;
X is hydrogen; or
(2) $R^1$ is a $C_2$ to $C_{25}$ alkylene, alkenylene or alkynylene linking group;
X is a group of formula —A—B wherein:
A is a linking group selected from —NR —, —COO—, —OCO—, —$CONR^6$—, —$NR^6CO$—, —N-H—CS—NH—and —S—S—wherein $R^6$ is selected from hydrogen and $C_1$ to $C_6$ alkyl;
B is a label; and
$R^2$ to $R^5$ are independently selected from $C_1$ to $C_6$ alkyl.

In the labelled PAF analogues of the invention of general formula I wherein X is hydrogen:
Preferred $R^1$ include straight $C_4$ to $C_{16}$ alkylene or alkenylene substituted by radioactive iodine.
Preferred $R^2$ to $R^5$ are methyl.

In the labelled PAF analogues of the invention of general formula I wherein X is a group of formula —A—B:

Preferred $R^1$ include straight chain $C_4$ to $C_{16}$ alkylene, alkenylene or alkynylene. More preferred $R^1$ include straight chain $C_4$ to $C_8$ alkylene.

Preferred A include $-NR^6-$, $-COO-$, $-OCO-$, $-CONR^6-$ and $-NR^6CO-$ and preferred $R^6$ include hydrogen and methyl. More preferred A include $-NR^6-$ and $-OCO-$.

In this specification, "label" is used to mean conventional labels used in immunoassay procedures including : the radioactive isotope labelled groups based on $^{125}$I-histamine, $^{125}$I-tyramine, $^{125}$I-tyrosine methyl ester and $^{125}$I-Bolton Hunter Reagent; enzymic labels; and photometric labels. Specific examples emzymic labels include horseradish peroxidase, alkaline phosphatase, beta-galactosidase and urease. Specific examples of photometric labels include fluorescent groups such as fluorescein and its derivatives, rhodamine and its derivatives, phycoerythrins, europium, "Texas Red", luminescent labels such as luminol and its derivatives, acridinium esters and umbelliferins.

Preferred $R^2$ to $R^5$ are $C_1$ to $C_3$ alkyl, especially methyl.

In another embodiment the invention provides compounds of general formula (I) which are useful as intermediates for the preparation of the antigenic PAF analogues of the invention wherein:

$R^1$ is a $C_2$ to $C_{25}$ alkylene, alkenylene or alkynylene linking group; and X is selected from the group consisting of formyl, carboxy, di($C_1$ to $C_6$ alkoxy)methyl, $N-C_1$ to $C_6$ alkylamino, N,N-di($C_1$ to $C_6$ alkyl)amino, hydroxy and mercapto.

In the intermediate compounds of the invention of general formula I:

Preferred $R^1$ include straight chain $C_4$ to $C_{16}$ alkylene, alkenylene and alkynylene. More preferred $R^1$ include straight chain $C_4$ to $C_8$ alkylene.

Preferred X include formyl, carboxy, dimethoxymethyl and hydroxy.

In another embodiment the invention provides a process for the preparation of compounds of general formula (I) which process comprises:

(a) reacting: a compound of general formula (II)

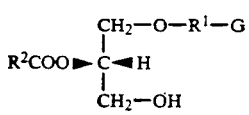

II wherein $R^1$ and $R^2$ are as hereinbefore defined and G is selected from di($C_1$ to $C_6$ alkoxy)methyl and groups which may be reacted, using conventional methods, to give a group selected from formyl, di($C_1$ to $C_6$ alkoxy)methyl, carboxy, amino, $N-C_1$ to $C_6$ alkylamino, N,N-di($C_1$ to $C_6$ alkyl)amino, hydroxy and mercapto;

a phosphorylation agent; and an N,N,N-tri($C_1$ to $C_6$ alkyl)ethanolamine derivative to give a compound of general formula (III)

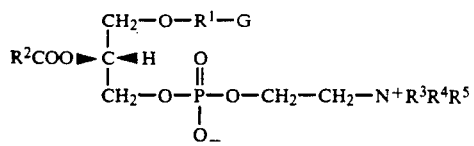

(b) reacting the product of (a) to convert group G as hereinbefore defined to a group selected from $N-C_1$ to $C_6$ alkylamino, N,N-di($C_1$ to $C_6$ alkyl)amino, hydroxy and mercapto and to introduce the desired group X.

In a specific example of the process for the preparation of compounds of general formula (I):

(a) a compound of general formula (II), wherein G is dimethoxymethyl, $R^1$ is selected from $C_4$ to $C_{16}$ alkylene, alkenylene and alkynylene and $R^2$ is methyl, is reacted with phosphorus oxychloride and choline tosylate to give a compound of formula (III), wherein G is dimethoxymethyl, $R^1$ is selected from $C_4$ to $C_{16}$ alkylene, alkenylene and alkynylene, and $R^2$ to $R^5$ are methyl; and (b) the product of (a) is reacted with acid to give a compound of formula (I) wherein X is formyl and $R^1$ to $R^5$ are as hereinbefore defined, which is reacted with a protein or synthetic peptide followed by reduction of the resulting imine to give a compound of general formula (I) wherein $R^1$ to $R^5$ are as hereinbefore defined and X is the group —A—B wherein A is the linking group $-NR^6-$ in which $R^6$ is hydrogen and B is a protein or synthetic peptide.

It will be recognized by those skilled in the art that in those antigenic PAF analogues of general formula I the group B may be monovalent or polyvalent such that a plurality of residues of general formula (I), typically between 1 and 500 and usually between 2 and 20, are attached to each group B. Therefore, in those antigenic PAF analogues of general formula (I) in which X is the group —A—B, if the residue of formula (I) is represented by Z then the invention includes antigenic PAF analogues of formula $(Z)_nB$ wherein n is an integer from 1 to 500.

It will also be recognized by those skilled in the art that certain of the PAF analogues of general formula (I) may be non-covalently bonded to or adsorbed onto a solid support. Accordingly in another embodiment the invention provides supported PAF analogues comprising PAF analogues of general formula (I) wherein:

(1) $R^1$ is a $C_2$ to $C_{25}$ alkylene or alkenylene linking group substituted by radioactive iodine;

X is hydrogen (2) $R^1$ is a $C_2$ to alkylene, alkenylene or alkynylene linking group optionally substituted by tritium or radioactive iodine;

X is selected from:

(a) the group consisting of formyl, di($C_1$ to $C_6$ alkoxy)methyl, carboxy, isothiocyanato, $N-C_1$ to $C_6$ alkylamino, N,N-di($C_1$ to $C_6$ alkyl) amino, hydroxy and mercapto; and (b) the group —A—B wherein A is a linking group selected from the groups $-NR^6-$, $-COO-$, $-OCO-$, $-NR^6CO-$, $-NH-CS-NH-$ and $-S-S-$ wherein $R^6$ is selected from hydrogen and $C_1$ to $C_6$ alkyl; and B is a label; and $R^2$ to $R^5$ are independently selected from $C_1$ to $C_6$ alkyl; non-covalently bonded to or adsorbed onto a solid support material.

Examples of solid support materials for said supported PAF analoques include proteins, synthetic polypeptides (e.g. polylysine) carbohydrates and carbohydrate derivatives [e.g. nitrocellulose, agaroses such as "Sepharose" (Trade Mark), and lipopolysaccharides] and synthetic polymers such as, for example, polysulphones, polyamides (e.g. polyacrylamide, nylon 6, nylon 66, nylon 610) and polystyrene in the form of particles, balls or formed articles such as test-tubes, rods, tubes, fins, wells, beads, disks, slides, plates and micro-tire plates.

Although PAF itself has been found to be insufficiently antigenic to produce the PAF-antibodies required to develop an immunoassay for PAF, surprisingly it has been found that:

(a) PAF adsorbed onto or non-covalently bound to a monofunctional or polyfunctional protein, peptide, carbohydrate, lipid or a derivative thereof of molecular weight at least 2000 and capable of eliciting an antigenic response; and (b) the antigenic PAF analogues of general formula (I); stimulate the production of antibodies which are antibodies to PAF. Accordingly in a further embodiment the invention provides antibodies to PAF and methods for their production. Such antibodies, hereinafter referred to as PAF-antibodies or anti-PAF, may be prepared by those techniques known in the art and conventionally involve introducing an antigenic PAF analogue of general formula (I) into an animal such as a rabbit, mouse, donkey, sheep, etc. to produce antibodies to the antigen and isolating and purifying the antibodies. The PAF-antibodies of the invention may be labelled with any of the conventional labels used in immunoassay procedures. Such labels include, for example, radioactive labels, enzymic labels and photometric labels such as those hereinbefore described.

The PAF antibodies of the invention include both monoclonal antibodies and polyclonal antibodies and techniques known in the art may be utilized to prepare the required type of antibody. For example, monoclonal antibodies may be produced using the antigenic PAF analogues of general formula (I) of the invention by the techniques taught by G. Kohler and C. Milstein, Nature,256, 495-497 (1975).

The PAF analogues and PAF antibodies of the invention may be used to qualitatively and quantitatively analyse for the presence of PAF in biological fluids. Accordingly in a further embodiment the invention provides methods for the immunoassay of PAF in biological fluids using the PAF analogues and/or PAF-antibodies of the present invention.

In one method PAF or PAF analogue is immobilised on a solid support and reacted with labelled or unlabelled PAF-antibodies in the presence of known amounts of competing free PAF to generate a graph showing percent inhibition versus PAF concentration. If, unlabelled PAF antibody is used the antibody bound which binds to the first is detected by using a labelled second antibody (goat, donkey, sheep, etc.). Using this graph the amount of free PAF in biological fluids may be quantitatively measured.

In another method, unlabelled anti-PAF bound to a solid support is reacted with a polyvalent antigenic PAF analogue of formula $(Z)_nB$ (e.g. PAF-polylysine). The resulting complex is then determined using labelled anti-PAF which binds to free PAF residues on the polyvalent antigenic PAF analogue.

In another method, unlabelled anti-PAF bound directly, either covalently or non-covalently, to a solid phase such as magnetized particles, plastic tubes, microtitre plates, "Sepharose" (Trade Mark) particles, polyacrylamide particles, nylon or polystyrene balls, etc. is mixed in a competition assay with: (a) a known quantity of labelled PAF; and (b) known quantities of unlabelled PAF contained in standard solutions or PAF to be measured in an extract or biological fluid. The concentration of unlabelled PAF in the sample is then determined from a standard curve, for example from a logit/log standard plot.

In another method, the procedure above is used except that the anti-PAF is linked to the solid phase by a ligand such as an antibody, protein A, lectin or an enzyme, for example:

solid phase/sheep (or some other species) anti-rabbit(or mouse etc.) immunoglobulin/rabbit (or mouse etc.) anti-PAF; and solid phase/protein A/rabbit (or mouse etc.) anti-PAF.

In another method, anti-PAF, labelled PAF and PAF to be measured are mixed and the free PAF and antibody-bound PAF are separated using dextran-coated charcoal or some other solid phase adsorbent such as hydroxyapatite etc. The concentration of unlabelled PAF in the sample being measured is then determined from a standard curve.

In another method, anti-PAF/PAF complexes are precipitated with a second antibody or with a protein precipitating reagent such as ammonium sulphate. Again, concentrations of unlabelled PAF may be determined from a standard curve.

In a further embodiment the invention also provides a kit for the immunoassay of PAF in a biological fluid said kit comprising PAF-antibodies of the present invention.

In practice, it has been found that the PAF present in biological fluids such as blood serum is rapidly degraded by the enzyme PAF-acetylhydrolase which is also normally present in blood serum. Therefore, it is preferable to first deactivate the enzyme. Three methods have been published for the deactivation of the enzyme, namely use of 1N hydrochloric acid, use of diisopropylfluorophosphate, and use of phenylmethanesulphonyl fluoride, but these methods suffer the disadvantages of use of drastic conditions and/or toxic substances.

It has now been found that the addition of a detergent to the biological fluid sufficently deactivates the enzyme to enable PAF to be quantitatively determined. Therefore, in a further embodiment the invention provides a method of immunoassay of PAF in biological fluid which comprises diluting the fluid with an aqueous detergent solution, prior to subjecting the diluted fluid to an immunoassay. Preferably the detergent is a nonionic detergent, such as those selected from the group consisting of: polyalkylene glycols; alcohol, phenol and alkylphenol alkoxylates; castor oil alkoxylates; the partial esters derived from long chain fatty acids and hexitol anhydrides and their alkoxylates; long chain alcohol polyglycol ether acetals; alcohol sugar acetals; and the lecithins. Detergents such as "Tween"20, "Nonidet" P40 and "Triton" X100 (Trade Marks) have been found particularly useful.

INDUSTRIAL APPLICABILITY

It will be evident to those skilled in the art that the products and methods of the invention find particular use in the medical and veterinary fields for the analysis of PAF.

PREFERRED EMBODIMENTS

Embodiments of the present invention will now be described by way of example only.

EXAMPLE 1

Preparation of 2-O-Acetyl-1-O-(6',6'-dimethoxyhexyl)-sn-glyceryl-3-phosphorylcholine

1. 1,1-Dimethoxycyclohexane

A mixture of cyclohexanone (52 ml, 0.5 mol), trimethylorthoformate (66 ml, 0.6 mol), methanol (51 ml, 1.26 mol) and concentrated $H_2SO_4$ (1 drop) was refluxed for 18 hours. A solution sodium methoxide in methanol was added until the mi was neutral, and the mixture was fractionally distilled. 1,1-Dimethoxycyclohexane was obtained from the fraction b.p. 162°–164° C. (50.6 g, 70%).

2. 1-Methoxycyclohexene 1,1-Dimethoxycyclohexane (25 g, 0.174 mol) was heated with p-toluenesulfonic acid (35 mg) at 140° C. for 3 hrs. Methanol was distilled off during the reaction. The residue was fractionally distilled, yielding 1-methoxycyclohexene (15.2 g, 80%) b.p. 144°–146° C.

3. Methyl 6,6-dilmethoxyhexanoate

A solution of 1-methoxycyclohexene (4.5 g, 0.04 mol) in methanol (140 ml) was ozonolysed at 0° C. until the uptake of ozone ceased. The solution was degassed and a suspension of reduced $Pd/CaCO_3$ (1.0 g) catalyst in methanol (30 ml) was added. The mixture was filtered through celite, and the filtrate was evaporated. Trimethylorthoformate (7 ml, 0.06 mol), methanol (5 ml, 0.12 mol) and conc.$H_2SO_4$ (1 drop) were added to the residue. After 17 hours, the mixture was neutralized with sodium methoxide solution and then fractionally distilled. Methyl 6,6-dimethoxyhexanoate was collected as the fraction b.p. 80°–90° C./1.0 mm (4.1 g, 54%).

4. 6 6-Dimethoxyhexan-1-ol

To a stirred mixture of lithium aluminium hydride (3.8 g, 0.1 mol1 in ether (80 ml) under nitrogen, was added methyl 6,6-dimethoxyhexanoate (15.0 g, 0.079 mol) in ether (50 ml) at a rate to maintain reflux (ca.1.5 hr). The mixture was further refluxed for 1.5 hrs., and then cooled to 0° C. Sodium hydroxide solution (13 ml, 7 M) was added dropwise while cooling in ice. After stirring for 1 hour, the mixture was filtered through a layer of magnesium sulfate. The residue was washed with ether, and the combined filtrates were evaporated. The residue was subjected to "suction" chromatography. 6,6-Dimethoxyhexan-1-ol was eluted with 25% ethyl acetate in light petroleum (10.3 g, 80%).

5. 2-O-Acetyl-3-O-benzyl-1-O-(6',6'-dimethoxyhexyl)-sn-glycerol

Sodium hydride dispersion (0.377 g, 12.6 mmol, 80% in oil) was washed with dry ether under nitrogen. The residue was resuspended in dry DMF (30 ml), and 6,6-dimethoxyhexan-1-ol (1.62 g, 10 mmol) was added. The mixture was heated at 80° C. for 1.25 hr., during which time the sodium hydride reacted. (R)-1-(Benzyloxy)-2,3-epoxypropane (1.64 g, 10 mmol) was added and heating was continued for 2 hr. Upon cooling, water (100 ml) was added and the mixture was extracted with ether (100 ml, 2×40 ml). The combined extracts were washed with water (2×80 ml) and brine (10 0 ml), dried ($MgSO_4$) and evaporated. The residual oil (2.8 g) was dissolved in chloroform (36 ml), and cooled to 0° C. Pyridine (3.5 ml, 43 mmol) and freshly distilled acetyl chloride (0.94 ml, 13.2 mol) were added. The mixture was stirred for 0.5 hr. at 25° C., then 2 hr. at room temperature (RT). Ice water (100 ml) was added and the layers separated. The aqueous layer was extracted with chloroform (2×40 ml), and the combined organic phases were washed with water (100 ml) and brine (100 ml), dried ($MgSO_4$) and evaporated. The residue was subjected to chromatography and the product was eluted with petroleum ether-ethyl acetate (9:1). Evaporation of this fraction yielded the product as a colorless oil (1.82 g, 50%) b.p. 170° C./0.2 mmHg ($C_{20}H_{32}O_6$ requires C, 65.19; H, 8.75%, Found: C, 65.06%; H,8.66%), $[\alpha]_D +1.98°$ (c 5.06, benzene). $^1$H N.M.R.$\delta$:7.36, m,5, ArH; 5.17,q,1,J 5.0 Hz, H2; 4.50,d,2,J 2.5 Hz, benzyl; 4.36, t,1,J 5.7 Hz, —CH-(OMe$_2$); 3.62d,2,J 5.0 Hz, H3; 3.58,d,2,J 5.2 Hz, OCH$_2$—; 3.48–3.39,m,2,H1; 3.31,s,6,OCH3; 2.12,s,3,COCH3; 1.72–1.26,m,8,—CH$_2$—. Mass spectrum: m/e 337, 305, 287, 245, 229, 215, 207, 146, 117, 113, 111, 91, 81, 75, 72.

6. 2-O-Acetyl-1-O-(6',6'-dimethoxyhexyl)-sn-glycerol

2-O-Acetyl-3-O-benzyl-1-O-(6',6'-dimethoxyhexyl)-sn-glycerol (369 mg, 1.0 mmol) was hydrogenated in THF (10 ml) over Palladium/carbon (14 mg, 10%) until the uptake of hydrogen ceased (approx. 2.5 hr.). The solution was filtered through celite, and the filtrate was evaporated to yield a colourless oil (278 mg, 100%) which was used immediately. $^1$H N.M.R.$\delta$: 5.04,q,1,J 5.0 Hz,H2; 4.40,t,1,J 5.7 Hz, —CH(OMe)$_2$; 3.84, d,2,J 5.0 Hz, H3; 3.65, d,2J 5.2 Hz, OCH$_2$—; 3.56–3.44 m 2 H1; 3.35 s 6 OCH3; 2.5,s(b),1,OH; 2.14,s,3, COCH3; 1.7–1.3,m,8, —CH$_2$—.

7. 2-O-Acetyl-1-O-(6', 6'-dimethoxyhexyl)-sn-glyceryl 3-phosphorylcholine

To a stirred, cold (0° C.) solution of distilled triethylamine (0.35 ml, 2.5 mmol) in dichloromethane(4 ml) under nitrogen, was added distilled phosphorous oxychloride (0.11 ml, 1.2 mmol) and then 2-O-acetyl-1-O-(6',6'-dimethoxyhexyl)-sn-glycerol (278 mg, 1.0 mmol) in dichloromethane (5 ml). The solution was stirred for 1 hr. at RT, and choline tosylate (465 mg, 1.7 mmol) in pyridine (10 ml) was added. Stirring was continued for 17 hrs. at RT. Sodium bicarbonate (0.4 g) and water (1 ml) were added and the mixture was evaporated at 30° C. The residue was extracted several times with chloroform (total 40 ml) and filtered. The filtrate was evaporated to yield a semi-solid residue (1.3 g).

An anion exchange column was prepared from DE-32 celluose (5.5 g) in acetic acid, and washed successively with methanol, methanol/chloroform (1:1) and chloroform. The mixture (1.3 g) was applied to the column in a small volume of chloroform, and was then eluted with chloroform (100 ml), then methanol in chloroform (100 ml each of 1.5%, 3%, 4.5%, 6% v/v). The product was contained in the fractions 3-6% methanol in chloroform, as determined by t.l.c. (CHCl$_3$/MeOH/-H$_2$O 60:35:5). Evaporation of these combined fractions yielded a pale yellow semi-crystalline material (0.21 g), which was contaminated with a tosylate salt (approx. 30%). $^1$H N.M.R.δ: 5.13,m,1,H2; 4.37,t,1,J 5.7 Hz,—CH(OMe)$_2$; 4.3–3.2,m,all other protons on C δ to O or N; 2.06, s,3, COCH$_3$; 1.7–1.3, m,8,—CH$_2$—. $^{13}$C N.M.R. δ170.49,s, C=O; 104.25, s, —CH(OMe)$_2$; 71.90,d,J 8.0 Hz, C2; 71.17,s,—CH$_2$O(or N); 69.00,s,—CH$_2$O(or N); 65.76,s,—CH$_2$O (or N); 63.76,d, J 5.1 Hz; —CH$_2$OP; 59.03,d,J 4.4 Hz, —CH$_2$OP; 53.78,s,—N+(CH$_3$)$_3$; 53.38,s,OCH$_3$; 32.24,s,—CH$_2$—;21.00,s, COCH$_3$.

EXAMPLE 2

Preparation of 2-O-Acetyl-1-O-(6'-oxohexyl)-sn-glyceryl-3-phosphorylcholine

Crude 2-O-acetyl-1-O-(6',6'-dimethoxyhexyl)-sn-glyceryl-3 phosphorylcholine (130 mg) was suspended in ethyl acetate (9 ml) and aqueous trifluoroacetic acid (TFA) (170μl, 90%) was added. The mixture was allowed to stand at RT for 1.5 hr. and 4° C. for 17 hrs., until the deprotection was complete by t.l.c. Toluene (9 ml) was added and the mixture evaporated. The residue was repeatedly evaporated from ethyl acetate/toluene (1:1) (10 ml) and alternatively from toluene (10 ml). The mixture was chromatographed on silica gel (70–230 mesh) and the product was eluted with CHCl$_3$/MeO/H$_2$O (40:60:10). Evaporation of the appropriate fractions yielded a colorless oil (50 mg). $^1$H N.M.R. δ: 9.78,t,1,J 2.0 Hz, CH=O; 5.1,m,1,H2; 4.4–3.2,m, all other protons on C δ to O or N; 2.46, dt,2,J 2.0 & 7.0 Hz, —CH$_2$—CHO; 2.08,s,3,COCH$_3$; 1.7–1.3,m,6,—CH$_2$—. $^{13}$C N.M.R.δ: 176.05,s, —CHO; 170.79,s, —OCOCH$_3$; 72.07,s,C2; 71.21,s,—CH$_2$O (or N); 69.27,s, —CH$_2$O (or N); 66.12,s, —CH$_2$O (or N); 64.11,s, —CH$_2$OP; 59.38,s, —CH$_2$OP; 54.20,s,—N+(CH$_3$)$_3$; 43.78,s,—CH$_2$CHO; 29.28,s,—CH$_2$—;25.64,s,—CH$_2$—; 21.80,s,—CH$_2$—; 21.26,s,COCH$_3$.

EXAMPLE 3

Coupling 2-O-acetyl-1-O-(6'-oxohexyl)-sn-glyceryl-3-phosphorylcholine to methylated BSA(PAF-BSA)

Methylated bovine serum albumin (250 mg) was dissolved in methanol (90 ml) and 2-O-acetyl-1-O-(6'-oxohexyl)-sn-glyceryl-3-phosphorylcholine (25 mg) in methanol (5 ml) was added. The solution was left at RT for 0.5 hr., and then sodium cyanoborohydride (100 mg) was added. The pH of the solution was adjusted to 5 with 1M HCl. After standing for 16 hr. at RT, the mixture was evaporated. The residue was dispersed in water (90 ml) and dialysed against distilled water (20 l). The dialysate was freeze-dried to yield a fluffy white material (238 mg). This material was assayed for phosphorous content, which was found to be 100 nanomoles per mg.

EXAMPLE 4

Coupling 2-O-acetyl-1-O-(6'-oxohexyl)-sn-glyceryl-3-phosphoryl-choline to polylysine (PAF-PL)

2-O-Acetyl-1-O-(6'-oxohexyl)-sn-glyceryl-3-phosphorylcholine was coupled to the polyvalent synthetic polypeptide polylysine following essentially the same procedure as that described in Example 3.

EXAMPLE 5

Inactivation of PAF-Acetylhydrolase

The following experiments demonstrate that PAF-acetylhydrolase can be deactivated by the addition of detergents.

Materials

PAF (from bovine heart lecithin) and "Tween" 20 (polyoxyethylene sorbitan monolaurate) were from Sigma (St. Louis, Mo., USA). Human sera albumin (HSA) was from Commonwealth Serum Laboratories (Melbourne, Australia).

Serum

Blood was collected from normal human donors by venipuncture, allowed to clot and the serum collected. Serum was stored at −20° C. until used. Similarily, rabbit serum was obtained from the ear veins of normal rabbits.

Platelet-Rich Plasma

Whole blood was collected from normal human donors, who had taken no medication for at least 10 days before venipuncture, and mixed with 0.1M trisodium citrate (0.1 vol). Platelet-rich plasma was produced by centrifugation (10 min, 600 r.p.m.) and was used within 1 hour.

Dilution of Sera

Sera were diluted 1 in 100 in either PBS or 0.1% "Tween" in PBS (v/v). Diluted acid-treated sera were prepared by mixing sera (1 vol.) with 0.1M citrate buffer pH 3.0 (2 vol.), and then 15 minutes later with PBS (98 vol.).

Determination of PAF-acetylhydrolase activity

Diluted serum (50μl) was incubated with 3.7×10$^{-6}$ M PAF (in 2.5% HSA) (50μl) for 27 hours at 25° C. The solution (50μl) was then tested for platelet aggregation activity at 37° C. in a Payton dual channel aggregometer using human platelet-rich plasma (500 μl).

RESULTS AND DISCUSSION

Two human sera and two rabbit sera, each with added PAF, were diluted by the three methods (PBS, "Tween" and acid-treated) and were then tested for acetylhydrolase activity. The results were in the form of light-transmission tracings from the aggregometer. After 27 hours incubation, PAF was destroyed in all sera diluted with PBS whereas the sera diluted in 0.1% "Tween" showed no inactivation of PAF. The "Tween"-diluted sera were tested for platelet aggregating activity, but no aggregation was observed. As a control for the above experiment, PAF was incubated with PBS or 0.1% Tween in PBS. In these experiments platelet aggregation activity was retained.

Disparity between human and rabbit sera was found when the sera were treated with acid. Whereas, rabbit sera no longer destroyed PAF, acid-treated human serum still had acetylhydrolase activity. Human and rabbit sera appear to have the same buffering capacity, so the disparity probably arises from varying acid-sensitivities of the two acetylhydrolases.

These results show that "Tween" 20 inactivates PAF-acetylhydrolase. Dilution in "Tween" is thus a simple and mild method of inactivating PAF-acetylhydrolase and this finding will be of great importance in immunoassay procedures used to measure PAF in biological fluids.

EXAMPLE 6

Preparation of PAF-antibodies

2-O-acetyl-1-O-(6'-oxohexyl)-sn-glyceryl-3-phosphorylcholine coupled to methylated bovine serum albumin prepared as described in Example 3 (PAF-BSA) was used as an antigen in rabbits and the immunoglobulin fraction was isolated from the rabbit anti-PAF serum produced by affinity chromatography on "Sepharose"/protein A.

The presence of PAF-antibodies in the isolated immunoglobin fraction was determined by a direct binding assay showing binding to tritium labelled PAF ($^3$H-PAF) as described below.

A sample of the immunoglobulin fraction (Ig) was mixed in an assay tube with a mixture (3–5mg) of "Sepharose" (solid support) and protein A (a ligand to link the antibody to solid support) and $^3$H-PAF in a total volume of 50 to 100 μl and incubated at room temperature overnight. The resulting mixture was centrifuged, washed twice with phosphate buffered saline containing 0.1% "Tween" 20, centrifuged and the sediment transferred in water (200 μl) to the liquid scintillant "Aquasol" (3 ml) and counted in a liquid scintillation counter.

The results, tabulated below, indicate significant uptake of $^3$H-PAF by the immunoglobulin isolated from rabbits treated with the PAF-BSA antigen in comparison to "normal" immunoglobulin isolated from control rabbits.

| Rabbit No | Ig (μg) | $^3$H-PAF (cpm) | Assay Count (cpm) | $^3$H-PAF Uptake (%) |
|---|---|---|---|---|
| 1 | 20 | 28,123 | 5,046 | 17.9 |
| 1 | 10 | 28,123 | 5,124 | 18.2 |
| 1 | 5 | 28,123 | 3,967 | 14.1 |
| 2 | 20 | 28,123 | 4,449 | 15.8 |
| 2 | 10 | 28,123 | 3,001 | 10.7 |
| 2 | 5 | 28,123 | 2,189 | 7.8 |
| Control | 20 | 28,123 | 326 | 1.2 |
| Control | 10 | 28,123 | 492 | 1.7 |
| Control | 5 | 28,123 | 281 | 1.0 |
| None | 0 | 28,123 | 140 | 0.5 |

*"Sepharose", "Tween" and "Aquasol" are Trade Marks.

EXAMPLE 7

The following experiments demonstrate the use of PAF-antibodies of the present invention in a competition or inhibition assay with a known quantity of labelled PAF and known quantities of unlabelled PAF or PAF analogues of the invention which ca be used to establish standard plots from which the quantity of PAF in sample can be determined. They also demonstrate the binding of the PAF-antibodies of the invention to PAF and the PAF analogues of the invention (e.g. PAF-PL of Example 4) in comparison to lyso-PAF, lecithin and lyso-lecithin.

A standard quantity of immunoglobulin containing PAF-antibodies (Ig) prepared as described in Example 6 was mixed in an assay tube with a mixture (3–5mg) of "Sepharose" and protein A, $^3$H-PAF (22,676 cpm), and a sample of a "test" substance for competitive binding to PAF-antibodies in a total volume of 100 to 200 μl and the mixture was incubated at room temperature overnight. The resulting mixture was centrifuged, washed twice with phosphate buffered saline containing 0.1% "Tween" 20, centrifuged and the sediment transferred in water (200 μl) to the liquid scintillant "Aquasol" (3 ml) and counted in a liquid scintillation counter.

The results, tabulated below, indicate:

(i) PAF-antibodies of the present invention may be used in a competition assay with known amounts of radiolabelled PAF and PAF to develop a standard plot for the quantitative determination of PAF by competition assay; and (ii) the specific binding of the PAF-antibodies of the invention to PAF and the PAF-analogues of the invention (e.g. PAF-PL)

| TEST SUBSTANCE | | ASSAY COUNT | ASSAY/ CONTROL |
|---|---|---|---|
| Name | ng | cpm | %* |
| PAF | 5,000 | 228 | 4.1 |
| PAF | 500 | 598 | 18.6 |
| PAF | 50 | 1,602 | 57.8 |
| PAF | 5 | 2,316 | 85.7 |
| PAF | 0.5 | 2,561 | 95.2 |
| PAF-PL | 27,000 | 435 | 12.2 |
| PAF-PL | 2,700 | 662 | 21.1 |
| PAF-PL | 270 | 429 | 11.9 |
| PAF-PL | 27 | 1,329 | 47.1 |
| PAF-PL | 2.7 | 2,338 | 86.5 |
| lyso-PAF | 5,800 | 2,746 | — |
| lyso-PAF | 580 | 2,744 | — |
| lecithin | 5,000 | 2,994 | — |
| lecithin | 500 | 2,545 | 99.6 |
| lyso-lecithin | 5,000 | 2,658 | 99.0 |
| lyso-lecithin | 500 | 2,668 | 99.4 |
| Control | 0 | 2,683 | 100.0 |
| No Ig | 0 | 123 | — |

$$* \frac{\text{Assay Count} - \text{Assay Count No Ig}}{\text{Assay Count Control} - \text{Assay Count No Ig}} \times 100$$

$$\text{i.e.} \frac{(\text{Assay Count} - 123) \times 100}{2560}$$

We claim:

1. A compound of general formula (I):

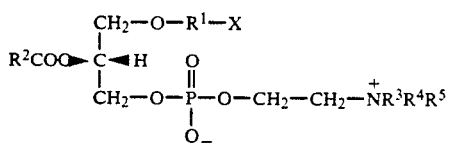

wherein:

(1) $R^1$ is a $C_2$ to $C_{25}$ alkylene or alkenylene linking group substituted by radioactive iodine;

X is hydrogen; or (2) $R^1$ is a $C_2$ to $C_{25}$ alkylene, alkenylene or alkynylene linking group optionally substituted by tritium or radioactive iodine;

X is selected from:

(a) the group -A-B wherein A is a linking group selected from the groups —NR$^6$—, —COO—, —OCO—, , —CONR$^6$—, —NR$^6$CO—, —N-H—CS—NH— and —S—S— wherein R$^6$ is selected from hydrogen and $C_1$ to $C_6$ alkyl;

and B is selected from:

(i) monofunctional and polyfunctional protein and peptide and derivatives thereof of molecular weight of at least 2000; and (ii) a label; and $R^2$ to $R^5$ are independently selected from $C_1$ to $C_6$ alkyl; and mixtures of the compound of formula I and its enantiomer.

2. Antigenic PAF analogues of general formula (I)

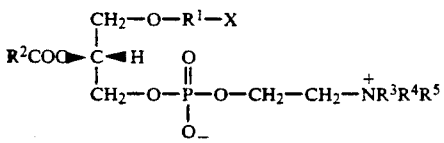

wherein:

$R^1$ is a $C_2$ to $C_{25}$ alkylene or alkynylene linking group;
X is the group —A—B wherein:
  A is a linking group selected from —$NR^6$—, —COO—, —OCO—, —$CONR^6$, —$NR^6CO$— and —S—S wherein $R^6$ is selected from hydrogen and $C_1$ to $C_6$ alkyl; and
  B is selected from monofunctional and polyfunctional protein and peptide derivatives thereof of molecular weight of at least 2000 which are capable of eliciting an antigenic response; and
$R^2$ to $R^5$ are independently selected from $C_1$ to $C_6$ alkyl.

3. Antigenic PAF analogues according to claim 2 wherein:
$R^1$ is selected from straight chain $C_4$ to $C_{16}$ alkylene;
X is a group —A—B wherein:
  A is selected from —$NR^6$—, —COO—, —OCO—, —$CONR^6$—and —$NR^6CO$—wherein $R^6$ is hydrogen or methyl; and
  B is selected from monofunctional and polyfunctional protein and peptide and derivatives thereof of molecular weight at least 5000 which are capable of eliciting an antigenic response; and
$R^2$ to $R^5$ are independently selected from $C_1$ to $C_3$ alkyl.

4. Antigenic PAF analogues according to claim 2 or claim 3 wherein:
$R^1$ selected from straight chain $C_4$ to $C_8$ alkylene;
X is a group —A—B wherein:
  A is selected from —NH—and —COO—; and
  B is selected from monofunctional and polyfunctional protein and peptide groups of molecular weight at least 10,000 which are capable of eliciting an antigenic response; and
$R^2$ and $R^5$ are each methyl.

5. Antigenic PAF analogues according to claim 2 wherein:

$R^1$ is hexylene;
X is a group —A—B wherein:
  A is —NH—; and
  B is selected from a protein residue derived from bovine serum albumin and a peptide residue derived from polylysine; and
$R^2$ to $R^5$ are methyl.

6. Labelled PAF analogues of general formula (I)

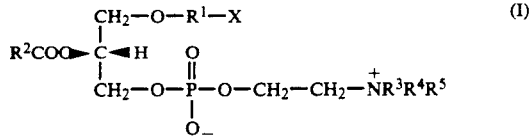

wherein
(1) $R^1$ is a $C_2$ to $C_{25}$ alkylene or alkenylene linking group substituted by radioactive iodine;
X is hydrogen; or
(2) $R^1$ is a $C_2$ to $C_{25}$ alkylene, alkenylene, or alkynylene linking group;
X is a group of formula —A—B wherein:
  A is a linking group selected from —$NR^6$—, —COO—, —OCO—, —OCO—, —$CONR^6$, —$NR^6CO$—, —NH—CS—NH—and —S—S— wherein $R^6$ is selected from hydrogen and $C_1$ to $C_6$ alkyl;
  B is a label; and
$R^2$ to $R^5$ are independently selected from $C_1$ to $C_6$ alkyl.

7. Labelled PAF analogues according to claim 6 wherein:
$R^1$ is selected from straight chain $C_4$ to $C_{16}$ alkylene;
X is a group of formula —A—B wherein:
  A is selected from —$NR^6$—, —COO—, —OCO—, —$CONR^6$—and —$NR^6CO$—wherein $R^6$ is hydrogen or methyl; and
  B is labelled group selected from: radiolabelled groups based on $^{125}$I-histamine, $^{125}$I-tyramine, $^{125}$I-tyrosine methyl ester and $^{125}$I-Bolton Hunter Reagent; enzymic labels; and photometric labels; and
$R^2$ to $R^5$ are independently selected from $C_1$ to $C_3$ alkyl.

8. An analogue according to claim 5 wherein B is bovine serum albumin.

* * * * *

UNITED STATES PATENT AND TRADEMARK OFFICE
CERTIFICATE OF CORRECTION

PATENT NO.   : 5,061,626
DATED        : October 29, 1991
INVENTOR(S)  : Baldo et al It is certified that error appears in the above-identified patent and that said Letters Patent is hereby corrected as shown below:

On the Title page, item [73], Assignee should read --

The University of Sydney of Sydney, Australia;

Macquarie University of New South Wales; and

Royal North Shore Hospital Area Health Service of

St. Leonards, New South Wales --.

Signed and Sealed this

Twentieth Day of July, 1993

Attest:

MICHAEL K. KIRK

*Attesting Officer*     *Acting Commissioner of Patents and Trademarks*